United States Patent [19]

Pickering

[11] 4,274,833
[45] Jun. 23, 1981

[54] NINHYDRIN REAGENT FOR USE IN AMINE AND AMINO ACID ANALYSES

[76] Inventor: Michael V. Pickering, 4081 Park Blvd., Palo Alto, Calif. 94306

[21] Appl. No.: 86,234

[22] Filed: Oct. 18, 1979

[51] Int. Cl.$^3$ .................. C09K 3/00; G01N 33/48; G01N 31/22; G01N 31/08
[52] U.S. Cl. .................. 23/230 B; 23/903; 23/230 M; 23/230 R; 252/408; 210/656
[58] Field of Search .............. 252/408; 23/230 B, 903, 23/230 M, 230 R; 210/31 C

[56] References Cited

U.S. PATENT DOCUMENTS

| | | | |
|---|---|---|---|
| 3,399,971 | 9/1968 | Kita | 23/230 B |
| 3,689,221 | 9/1972 | Udenfriend | 252/408 |
| 3,853,473 | 12/1974 | Morin et al. | 23/230 B |
| 3,912,655 | 10/1975 | Shukla et al. | 23/230 B |

OTHER PUBLICATIONS

Moore, S., J. Biol. Chem., vol. 243, No. 23, pp. 6281–6283 (1968).
Moore, S., et al. J. Biol. Chem., vol. 211, pp. 893–913 (1954).
Takahashi J. Biochem., vol. 83, p. 57 (1978).
Moore, S., et al. J. Biol. Chem., vol. 192, pp. 663–681 (1951).
Moore, S., et al. J. Biol. Chem., vol. 176, p. 367 (1948).

*Primary Examiner*—Teddy S. Gron
*Attorney, Agent, or Firm*—Bertram I. Rowland

[57] ABSTRACT

A ninhydrin reagent is provided for use in automatic analyzers which employs sulfolane as the water miscible organic solvent. The solution is buffered with lithium acetate and contains a small amount of hydrindantin as a stabilizer. The reagent is substantially colorless, exhibits great thermal and pH stability, longer shelf life, and in an automatic analyzer results in better signal to noise ratio, flatter base lines and better resolution of peaks.

3 Claims, No Drawings

NINHYDRIN REAGENT FOR USE IN AMINE AND AMINO ACID ANALYSES

BACKGROUND OF THE INVENTION

1. Field of the Invention

Quantitative and qualitative determination of amino acids in protein hydrolysates, body fluids and other physiological samples, is normally accomplished by employing ion-exchange chromatography using a cationic or anionic exchanger column. The analyte is placed on the column at a pH of about 3, at which pH the individual amino acids are positively charged. The column is then developed by gradually increasing the pH and ionic strength of the buffers with which the column is eluted.

As the column is developed, the acidic amino acids are removed from the resin first, followed by the neutral amino acids, and finally by the basic amino acids. As the amino acids are eluted from the column, they are reacted with ninhydrin or a fluorescer and the resultant color or fluorescence intensity is measured spectrophotometrically. Several automatic amino acid analyzers are commercially available which automatically separate the amino acids on an ion exchange column, contact the separated amino acids with ninhydrin, heat the mixture to develop the color, record the color intensity, at selected wavelengths, usually 440 nm and 570 nm, and plot the intensity on a graph. The identity of each amino acid is established on the basis of its migration characteristics and thus its position on the chromatogram; and the amount of amino acid is estimated quantitatively on the basis of the area under each peak of the curve as compared to that of a standard mixture.

In the development of a ninhydrin reagent for use in the automatic amino acid analyzers, there are several factors that need to be considered. Ninhydrin is not very soluble in aqueous media and solutions of ninhydrin are very unstable under normal experimental condition being highly susceptible to oxidation. For practical purposes the reagent must include a water miscible, preferably colorless organic solvent which solubilizes the hydrindantin and ninhydrin, as well as the blue compound (diketohydrindylidenediketohydrindamine) formed by the reaction of ninhydrin with amino acids.

The organic solvent used should be nontoxic to avoid expensive ventilation. Also, the solvent should not react with any of the solution components or products. In addition, during use of the reagent, precipitation of any of the components must be avoided or lines in the analyzer will become clogged. The available ninhydrins all have one or more shortcomings.

It would therefore be desirable to develop a ninhydrin reagent which would be stable to oxidation, which would exhibit pH and thermal stability, and a long shelf life. During analysis the reagent should provide flat base lines, sharp resolution, and good reproducibility of results.

2. Description of the Prior Art

Moore (J. Biol. Chem. 243, 6281 (1968)) teaches the use of aqueous dimethyl sulfoxide as a solvent for the ninhydrin reagent. Takahashi (J. Biochem. 83, 57 (1978)) teaches the use of sodium borohydride, in the preparation of a ninhydrin reagent, to prevent the formation of precipitates in the flow lines of the analyzer. Moore and Stein (J. Biol. Chem. 211, 907 (1954)) used methyl cellosolve (the monomethyl ether of ethylene glycol) as the organic solvent in ninhydrin reagents. The Merck Index, 8th Ed. lists sulfolane as an organic liquid which at 30° C. is miscible with water and is used as a selective solvent for liquid-vapor extractions.

SUMMARY OF THE INVENTION

An improved ninhydrin reagent and an improved method for amino acid analysis are provided which involve an aqueous sulfolane solution of ninhydrin. The solution is conventionally buffered and may contain other conventional additives. The improved ninhydrin reagent provides for long shelf life without observable discoloration so that a more sensitive amino acid analysis is achievable. The reagent is also relatively nontoxic, colorless, easily handled and in use in an analyzer does not form precipitates in the flow lines, a problem which has heretofore existed with prior art ninhydrin solutions.

DESCRIPTION OF THE SPECIFIC EMBODIMENTS

The subject invention is a novel storage stable ninhydrin reagent for the determination of amino acids and amines, employing sulfolane as a solubilizing solvent in an aqueous ninhydrin reagent. Conventionally, in addition to water and ninhydrin, ninhydrin reagent contains a reduced form of ninhydrin (hydrindantin) in minor amount as a stabilizer, which may be added to the mixture or prepared in situ by reducing a minor portion of the ninhydrin with a reducing agent. Normally, a buffer is also included in the medium, so that the pH remains constant during storage and use.

By employing sulfolane as the solubilizing agent, numerous advantages accrue, since the resulting ninhydrin reagent has long storage life without deterioration or color formation. In addition, the reagent is stable during use in an automatic analyzer. Thus, the concentration of the ninhydrin reagent remains constant and an undesirable background signal is not created by undesired reactions of the ninhydrin. This provides for better resolution and a more accurate quantitative determination in analyzing mixtures of amino acids and/or primary or secondary amines. Also, under the stressing conditions of automatic analyzers, the reagent is stable for long periods of time without precipitation resulting in the clogging of flow lines, when dismantling may be required to clear the flow line.

The ninhydrin reagent will generally have at least about 0.5 parts of sulfolane per part of water and not more than about 1.5 part of sulfolane per part of water, generally having at least about 0.6 part and preferably at least about 0.75 part and not more than about 1.2 part of sulfolane per part of water, all parts being by weight. The ninhydrin will generally be present in the solution at a concentration of at least about 0.5 weight percent and not more than about 2 weight percent, conveniently normally being at about 1 weight percent. The amount of reduced ninhydrin (hydrindantin) will generally be from about 0.5 to 2 weight percent of the ninhydrin, therefore generally being from about 0.01 to about 0.04 weight percent of the reagent solution.

The buffer which is employed is generally conventional and the concentration may be varied widely, depending upon the particular buffer employed. Various buffers include lithium acetate, sodium acetate, or the like, lithium acetate being preferred. The amount of buffer which includes the salt and acid will generally be at least about 10 weight percent, more usually about 15 weight percent, and preferably less than about 35 weight percent, more usually being from about 15 to 22 weight percent of the reagent solution. The reagent solution may be readily prepared in conventional ways. The reagent is normally prepared in an inert container, either plastic or glass, such as polypropylene, polyethylene or borosilicate glass. The preparation is conveniently carried out at ambient temperatures. Any heat which results from reactions or heats of solution may be readily dissipated by cooling. Deionized water should be employed.

While maintaining an inert atmosphere, such as nitrogen, argon, or the like, water is added with stirring, followed by the components of the buffer system, which are desirably prepared in situ. For example, lithium hydroxide is initially dissolved, followed by glacial acetic acid. After cooling to room temperature, the sulfolane is added followed by the ninhydrin. When this solution is substantially complete, hydrindantin may be added or an appropriate reducing agent added, such as sodium borohydride or stannous chloride, to provide the desired amount of hydrindantin. The resulting reagent may then be filtered, conveniently through a 0.45μ filter and then bottled in an inert atmosphere.

In a particular preparation, while maintaining continuous agitation into 200 ml of deionized water was dissolved 56 g of lithium hydroxide monohydrate, followed by the addition of 145 ml of glacial acetic acid. After cooling to room temperature, 200 ml of sulfolane was added followed by the addition of 10 g of ninhydrin after a few minutes. After 15 mins of stirring, 0.18 g of hydrindantin was added and stirring was continued until dissolution was complete to provide approximately 500 ml of solution. The reagent was then filtered through a filter of 0.45μ rating and bottled under nitrogen.

In order to demonstrate the many advantages of the use of sulfolane as a solubilizing solvent in a ninhydrin reagent, reagent prepared as described above was stored at room temperature. The lifetime of the reagent without any observable color production was at least three months. Furthermore, it was found that excellent reproducibility was achieved for repetitive analysis of a given sample with a given batch of reagent.

In automatic amino acid analyzers, frequently high temperatures and relatively long dwell times are involved for the ninhydrin reagent. For example the Beckman/Spinco Analyzer employs a 100° C. reaction temperature with a five minute dwell time. The Dionex automatic analyzer uses a 135° C. reaction temperature with a 1.5 min dwell time. As compared to other ninhydrin reagents, the subject reagent is usable at the elevated temperature.

A number of protein hydrolysates were determined using a reagent composition prepared as described above and a commercial automatic amino acid analyzer. The instrument settings and preparation were in accordance with manufacturer's instructions. The instrument was initially calibrated with a standard sample mixture containing known amounts of the various amino acids. Calibrations were repeated from time to time during the course of each experiment to insure instrumental and reagent stability. Buffer solutions were 0.1 M either in sodium acetate or sodium citrate and 0.9 M in sodium chloride. The pH of the eluting solution was varied from about 2.6 to about 7.5 for separation of the amino acids.

The ninhydrin reagent was pumped from the reagent reservoir at a rate of 1-2 ml/hr and mixed with the eluent from the ion exchange column, in a T-mixing valve situated just below the column. A temperature of 130° C. was employed with a dwell time of 1.5 min for developing the blue color. The color intensity resulting from the reaction of the ninhydrin reagent with the amino acids was monitored at 440 nm and 570 nm and the results automatically plotted as well as printed.

Several repetitive scans were obtained to verify the highh reproducibility of the results and the stability of the reagent. Concentrations of amino acids in the standard mixtures would vary from about 10 pM/l to 10 nM/l and could be detected over the entire range.

In a comparison of the subject reagent with the commercially available Moore's ninhydrin-DMSO reagent (Moore, supra) the subject reagent exhibited no background, even when stored over one month under ambient conditions, while the DMSO reagent contributed a substantial background, even when freshly prepared.

It is evident from the above results, that the compositions of the subject invention provide surprising and unique advantages over prior art ninhydrin reagent compositions. Not only do the compositions provide greatly extended storage stability as well as stability in use at elevated temperatures, but because of the relative absence of color development, greatly enhanced sensitivity and reproducibility is achieved in the analysis of amino acids and amines.

It is noted, that the total signal observed is somewhat lower than (about 70% of) the signal observed with Moore's DMSO based reagent. However, because of the greatly enhanced stability of the base line of the graph, an improved signal to noise ratio is obtained, which provides for the same or better minimum detection limit as the DMSO reagent, in addition to the numerous other advantages already indicated. Quite surprisingly, sulfolane is compatible with all of the reactants and the ninhydrin reagent, as well as amino acids and amines so as to allow for smooth and rapid reaction between ninhydrin and the amino groups. At the same time, the sulfolane solution does not result in undesirable discoloration and precipitation of the ninhydrin or products of ninhydrin reactions.

Although the foregoing invention has been described in some detail by way of illustration and example for purposes of clarity of understanding, it will be obvious that certain changes and modifications may be practiced within the scope of the appended claims.

What is claimed is:

1. A buffered aqueous ninhydrin reagent having from about 0.5 to 2 weight percent of ninhydrin, sulfolane and water at a ratio of from at least about 0.5 parts to not more than 1.5 part by weight of sulfolane per part of water, said reagent having a pH in the range of about 3 to 9.

2. A composition according to claim 1, wherein said buffer is lithium acetate and a sufficient amount of hydrindantin is present to act as a stabilizer.

3. In a method for analyzing an analyte which is one or a mixture of amino acids, primary or secondary amines, employing an ion exchange column and reacting the eluent from said ion exchange column with ninhydrin to reagent produce a colored product whose concentration is related to the amount of analyte in said eluent, and monitoring the light absorption of said colored product in said eluent, the improvement which comprises employing as a ninhydrin reagent for production of such color, a composition according to claim 1.

* * * * *